(12) United States Patent
Burghardt et al.

(10) Patent No.: US 6,521,402 B1
(45) Date of Patent: Feb. 18, 2003

(54) CRYOPRESERVATION OF TISSUES FOR USE IN NUCLEAR TRANSFER

(75) Inventors: Robert C. Burghardt, College Station, TX (US); Mark Westhusin, College Station, TX (US); Dana Dean, Bryan, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 09/882,474

(22) Filed: Jun. 14, 2001

Related U.S. Application Data
(60) Provisional application No. 60/211,862, filed on Jun. 14, 2000.

(51) Int. Cl.⁷ .................................................. A01N 1/02
(52) U.S. Cl. ........................ 435/1.3; 435/1.1; 435/1.2
(58) Field of Search ............................ 435/1.1, 1.2, 1.3

(56) References Cited

U.S. PATENT DOCUMENTS

| | | | |
|---|---|---|---|
| 4,559,298 A | 12/1985 | Fahy .............................. | 435/1 |
| 5,118,512 A | 6/1992 | O'Leary et al. ............. | 424/549 |
| 5,328,821 A | 7/1994 | Fisher et al. .................. | 435/1 |
| 5,891,617 A | 4/1999 | Watson et al. ............... | 435/1.3 |
| 5,964,096 A | 10/1999 | Watson et al. ................. | 62/78 |

FOREIGN PATENT DOCUMENTS

| WO | WO 92/0059 | 1/1992 |
|---|---|---|

OTHER PUBLICATIONS

Abir et al., "Preservation of fertility in women undergoing chemotherapy: Current approach and future prospects," *Journal of Assisted Reproduction and Genetics*, 15(8):469–477, 1998.

de Kanter et al., "A rapid and simple method for cryopreservation of human liver slices," *Xenobiotica*, 28(3):225–234, 1998.

Gianaroli et al., "Diagnostic testicular biopsy and cryopreservation of testicular tissue as an alternative to repeated surgical openings in the treatment of azoospermic men," *Hum Reprod.*, 14(4):1034–1038, 1999.

Oktay et al., "Cryopreservation of immature human oocytes and ovarian tissue—an emerging technology?" *Fertility and Sterility*, 69(1):1–7, 1998.

Sheridan et al., "Autologous skin banking," *Burns*, 24:46–48, 1998.

Simione, Cryopreservation Manual, Nalge Nunc Internation Corporation, Rochester, New York, 1998.

Sommer et al., "Cell cultures form cryopreserved renal biopsies and other tissue samples," *Exp. Toxic Pathol*, 51:229–234, 1999.

Wusteman et al., "Cryopreservation studies with porcine corneas," *Curr Eye Res*, 19(3):228–233, 1999.

Zieger et al., "Osmotic tolerance limits of canine pancreatic islets," *Cell Transplant*, 8(3):277–284, 1999.

*Primary Examiner*—Jean C. Witz
(74) *Attorney, Agent, or Firm*—Fulbright & Jaworski L.L.P.

(57) ABSTRACT

This relates to methods to minimize the growth of cells until such time as cells are needed for the nuclear transfer. This method can be used for processes in which cells need to be preserved by cryopreservation.

21 Claims, 2 Drawing Sheets

CRYOPRESERVATION OF TISSUES FOR USE IN NUCLEAR TRANSFER

The present application claims the benefit of U.S. Provisional Application Serial No. 60/211,862 filed on Jun. 14, 2000. The entire text of the above-referenced disclosure is herein incorporated by reference.

BACKGROUND OF THE INVENTION

1. Field of the Invention

The invention relates to the method of cryopreservation of biological tissues. It is particularly related to minimizing the amount of cell division for cells that will be used for the purpose of somatic cell nuclear transfer, while providing cells in which to test cell viability.

2. Background of the Invention

All documents referenced herewith are incorporated by reference. Regarding prior knowledge, cryopreservation of tissues for subsequent use in a number of applications has been reported. For example, cryopreservation of ovarian tissue is a promising technique for preserving fertility in cancer patients who are at risk of sterilization from radiation and/or chemotherapy treatment or for safeguarding reproductive potential of endangered species (Oktay et al., 1998; Abir et al., 1998). Cryopreservation of other tissue types such as skin (Sheridan et al., 1998), kidney (Sommer et al., 1999), liver (de Kanter et al., 1998), corneas (Wusteman et al., 1999), pancreatic islets (Zieger et al., 1999), and testicular tissue (Gianaroli et al., 1999) have also been reported.

The purpose of the invention is to minimize cell division until such time as cells are needed for the nuclear transfer. This method will be useful for any process in which cells need to be preserved by cryopreservation but also need to be tested for various factors. The method would provide an economic benefit by limiting the labor, supplies costs, and storage costs of generating a large amount of cells prior to the time when they are needed. The method provides a reduction in time that tissues are in the culture dish and allowed to explant cells before cryopreservation.

Cryopreservation methods include rapid vitrification (30,000° C./minute), slow vitrification (8,000° C./minute), rapid freezing (100° C./minute), and slow freezing (0.5° C./minute). The method of cryopreservation used is important due to the freezing of intracellular water. During slow cooling, water leaves the cell because of the osmotic imbalance caused by the lower concentration of water in the extracellular environment due to ice formation. The increase in solute concentration due to the decrease in water volume can be harmful. Alternatively, too much water in the inside the cell can lead to damage during warming. Cryoprotectants protect cells by diluting salt that becomes more and more concentrated as ice forms. They also stabilize membranes and proteins and reduce the intracellular ice formation temperatures. Cell survival is low at very slow and very fast cooling rates (U.S. Pat. No. 5,891,617).

Dimethylsulfoxide (DMSO) and glycerol are the most commonly used cryoprotectants. DMSO causes a depression in the freezing point and therefore increased water removal from the cell prior to freezing. DMSO generates heat when dissolved in aqueous solutions. It must be diluted and allowed to cool before addition to cells. DMSO and glycerol are usually used in a 5–10% solution in growth medium. They are not used together except for cryopreserving plant cells. Cells may be incubated in the cryoprotectant before beginning the cooling process. This is called the equilibration period. Cooling rates of 1° C. per minute and the use of a cryoprotective agent are commonly used to protect the cells. Larger cells generally require greater control of cooling rates. Frozen cells should be maintained below −130° C.

When thawing of the sample is desired, warming should occur as quickly as possible. This is generally achieved by placing the vial into 37° C. water. The outside of the vial is disinfected before the vial is opened to protect against contamination of the sample. The cells are then transferred to fresh growth medium to decrease the concentration of the cryoprotectant. The cells can be centrifuged and the supernatant removed. The cells are then resuspended in fresh growth medium (Simione, F. P., 1998).

PCT Patent Application No. PCT/US92/00599 describes a tissue preservation method in which dissected heart valve, veins and musculoskeletal connective tissue are divided into at least two portions that are contaminated with microbes to various degrees. The group containing a lower level of contamination is exposed to an antimicrobial regimen and cryopreserved. The group containing the higher level of contamination is exposed to a second antimicrobial regimen and cryopreserved. This reference is directed to the decrease of microbial contamination of heart valves, veins and musculoskeletal connective tissue. The antimicrobial regimen lasts preferably 4 hours.

U.S. Pat. No. 5,891,617 describes cryopreservation of harvested mammalian tissues and cultured tissue equivalents in a cryoprotectant solution. Solutions contain a cell penetrating glass forming agents such as propylene glycol, ethylene glycol, and dimethylsulfoxide or non-cell penetrating glass forming agents such as high molecular weight complex carbohydrates. These solutions are diluted in a base at physiological pH. The preferred solution is 2 M glycerol in Dulbecco's Modified Eagle's Medium (DMEM).

U.S. Pat. No. 5,964,096 describes a method and package design for cryopreservation and storage of cultured tissue equivalents. The cryopreservation method includes immersing the tissue in cryoprotectant solution, agitating the sample, cooling to solid-liquid phase equilibrium temperature for the cryoprotectant, seeding extracellular ice, and freezing the tissue to a temperature below −70° C. Cryopreserved tissue is warmed at a high rate by direct application of a warmed media or buffered solution or other heating method. Cryoprotectant is removed form the thawed tissue before use. Also described is a package that has an improved heat transfer rate, allowing for a more controlled cooling and heating process.

U.S. Pat. No. 5,328,821 describes methods and solution for the preservation of tissue. Particularly it relates to methods and solutions for preserving human tissue slices. Preservation solutions of this invention contain a sufficient amount of glucose to maintain the metabolic functions of the cells but not enough to stimulate acidosis.

U.S. Pat. No. 5,118,512 describes a process for cryopreserving bone with a cryopreservation agent and an agent to increase diffusion of the cryopreservation agent into the biological material.

U.S. Pat. No. 4,559,298 describes a method for the cryopreservation of biological materials by cooling the biological material to a vitreous state under pressure in the presence of an aqueous vitrification solution.

The present invention provides a method to both test the viability of the cells and protect cells from aging due to cell division. In addition, the present method also provides a method of obtaining a large number of cells from a single sample without exposing all of the cells to excessive cell division.

SUMMARY OF THE INVENTION

An embodiment of the present invention is a process for preserving viable tissues and cells comprising; obtaining a tissue specimen; dividing the tissue specimen into at least 2 portions; cryopreserving directly at least one portion of the tissue to minimize cell division; culturing at least one remaining portion or portions of tissue specimen in order to propagate cells and verify their viability; and cryopreserving cells obtained from tissue outgrowths or passage; and cryopreserving the cultured tissue portion or portions once the desired amount or number of cells have been obtained through outgrowth or passage. The use of the phrase "outgrowth or passage" means "outgrowth and/or passage," since the term "or" is not intended to be exclusive. The term "directly" means that an action is taken without performing any substantive process prior to taking that action, for example, "cryopreserving directly" means not doing any other step than those to achieve cryopreservation. It is contemplated that the tissue may be divided into 2, 3, 4, 5, 6, 7, 8, 9, 10, 11, 12, 13, 14, 15, or more portions, and that at least one portion is cryopreserved directly or prior to cell division taking place.

In another embodiment, the cryopreservation of cultured tissue occurs simultaneously with the cryopreservation of the cells. The term "simultaneously" means at the same time, that is, less than an hour within each other. In yet another embodiment, the cryopreservation of cultured tissue occurs after the cryopreservation of the cells. The cryopreservation of cultured tissue may occur more than 1, 2, 3, 4, 5, 6, 7, 8, 9, 10, 11, 12 hours, or 1, 2, 3, 4, 5, 6, 7 days, or 1, 2, 3, 4, 5 weeks, or 1, 2, 3, 4, 5, 6 months after the cryopreservation of the cells obtained from tissue outgrowths or passage.

In another embodiment, the process for preserving viable tissues and cells is for use in nuclear transfer. The tissue preserved may be that of a domestic, exotic, or food animal. In a further embodiment it is that of a mammal. More specifically, the tissue may be that of a dog, cat, horse, sheep, goat, or cow and most specifically that of a dog or cat.

In still another embodiment, the process for preserving viable tissues and cells may include an embodiment where tissue portions constituting the directly cryopreserved tissue and cultured tissue are less than or about 1 millimeter$^3$ pieces or portions.

In another embodiment, the process for preserving viable tissues and cells may include the cells or tissues to be cryopreserved being placed in a medium comprising less than or equal to 95% Basal Medium Eagle (BME), Dulbecco's Modified Eagles Medium (DME), Nutrient Mixture Ham's F-10, Nutrient Mixture Ham's F-12, Dulbecco's Modified Eagles Medium Nutrient Mixture F-12 Ham (DME/F12 1:1 mixture), L-15 Medium Leibovitz, McCoy's 5A Medium, Medium 199, Minimum Essential Medium Eagle (MEM), RPMI-1640 Medium, or Waymouth's Medium. More specifically, the medium may further comprise from about 5–20% Fetal Bovine Serum, at least 100 Units/milliliter penicillin, at least 0.1 milligrams/milliliter streptomycin, at least 0.25 micrograms/milliliter amphotericin B, and 10%–20% dimethylsulfoxide.

In another embodiment, the process for preserving viable tissues and cells may include placing the tissues in said medium for about 10 minutes before cryopreservation.

In another embodiment, the process for preserving the cells may include placement in said medium directly before cryopreservation.

In another embodiment, the tissues or cells are frozen at a rate of about –1° C./min. In yet another embodiment, the tissues or cells may be placed in an –80° C. freezer overnight and transferred into liquid nitrogen the next day. It is contemplated that the "next day" refers to an amount of time greater than 8 hours. In still another embodiment, after initial cryopreservation and before thawing is desired, the temperature of said tissue or cells may not exceed –60° C.

In another embodiment, the process for preserving viable tissues and cells may include placing cells or tissues to be cultured in a medium comprising less than or equal to 95% Basal Medium Eagle (BME), Dulbecco's Modified Eagles Medium (DME), Nutrient Mixture Ham's F-10, Nutrient Mixture Ham's F-12, Dulbecco's Modified Eagles Medium Nutrient Mixture F-12 Ham (DME/F12 1:1 mixture), L-15 Medium Leibovitz, McCoy's 5A Medium, Medium 199, Minimum Essential Medium Eagle, RPMI-1640 Medium, or Waymouth's Medium. More specifically, the medium may further comprise from about 5–20% Fetal Bovine Serum, at least 100 Units/milliliter penicillin, at least 0.1 milligrams/milliliter streptomycin, and at least 0.25 micrograms/milliliter amphotericin B. The medium may comprise about 10% Fetal Bovine Serum, at least 100 Units/milliliter penicillin, at least 0.1 milligrams/milliliter streptomycin, and at least 0.25 micrograms/milliliter amphotericin B.

In another embodiment, a process for tissue decontamination may be included in the preserving of viable tissues and cells comprising: incubating tissues in an about 1:30 chlorhexidine solution for not more than about 3 minutes; agitating tissues during the incubation period; placing tissues into a medium comprising Ham's F-12 and at least 600 Units/milliliter penicillin, at least 5 milligrams/milliliter streptomycin, and at least 1.5 micrograms/milliliter amphotericin B.; soaking tissues for about 40 minutes at about 4° C.; and proceeding with tissue isolation procedures, for example, as described herein.

In yet another embodiment, an apparatus for shipping tissue specimens to be preserved by the process above may be used with the apparatus comprising sterile tubes containing a sterile media storage solution, an insulated shipping container, and ice packs. The apparatus may further include sterile media comprising less than or equal to 95% Basal Medium Eagle (BME), Dulbecco's Modified Eagles Medium (DME), Nutrient Mixture Ham's F-10, Nutrient Mixture Ham's F-12, Dulbecco's Modified Eagles Medium Nutrient Mixture F-12 Ham (DME/F12 1:1 mixture), L-15 Medium Leibovitz, McCoy's 5A Medium, Medium 199, Minimum Essential Medium Eagle, RPMI-1640 Medium, or Waymouth's Medium. More specifically, the sterile media may further comprises from about 5–20% Fetal Bovine Serum, at least 100 Units/milliliter penicillin, at least 0.1 milligrams/milliliter streptomycin, and at least 0.25 micrograms/milliliter amphotericin B.

In still another embodiment, a method for maintaining tissue viability while transferring biological specimens to be preserved by the process above, may comprise receiving a storage box, refrigerating tubes of sterile storage solution, placing tissues in the tubes, and shipping to destination overnight in said storage box containing frozen ice packs.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF SUMMARY OF THE DRAWINGS

The following drawing forms a part of the present specification and is included to further demonstrate certain aspects of the present invention. The invention may be better understood by reference to the drawing in combination with the detailed description of specific embodiments presented herein.

DETAILED DESCRIPTION OF THE PREFERRED EMBODIMENT

Figure 1:
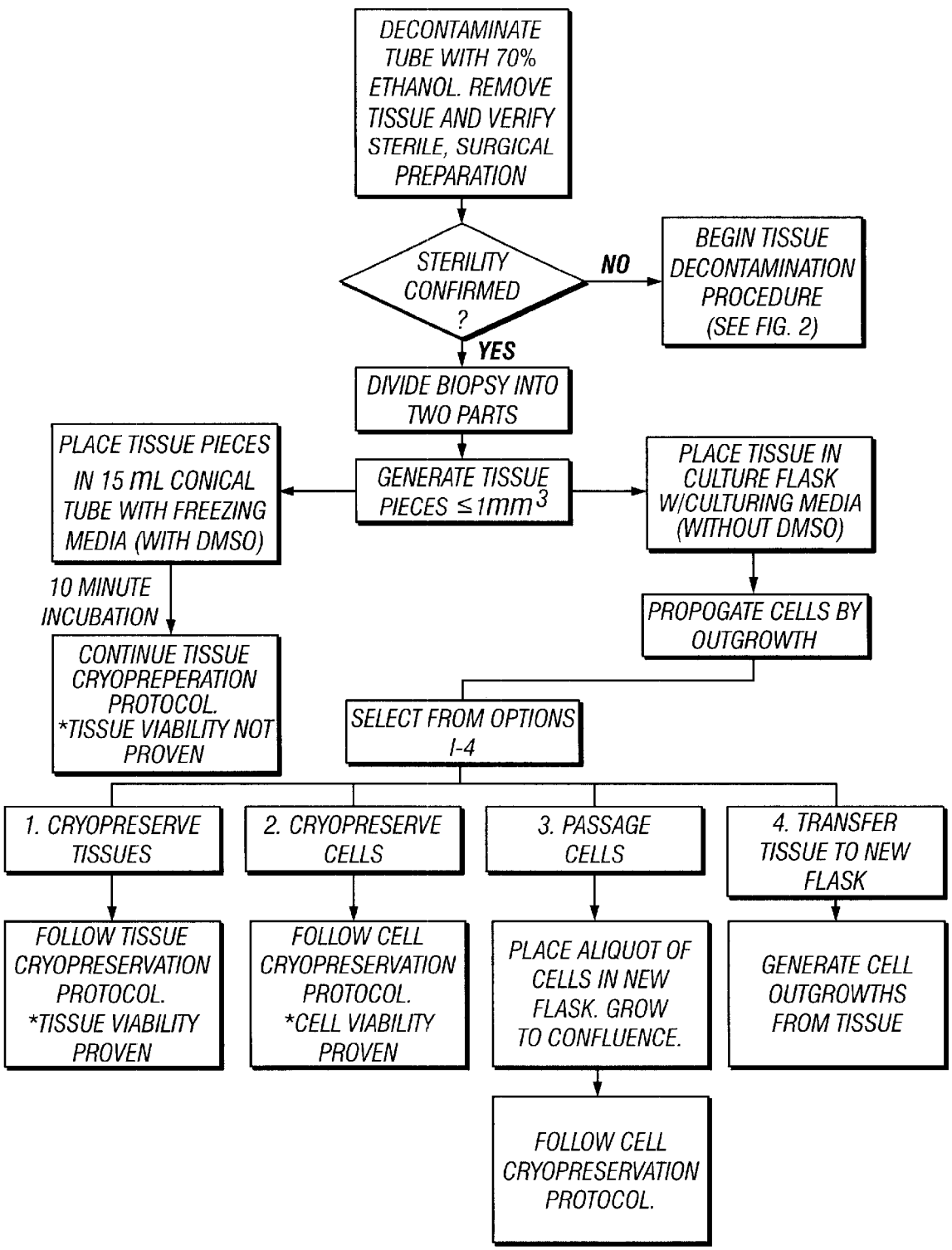
FIG. 1 Diagram of cryopreservation protocol.

This technology represents a strategy to minimize the continuous proliferation (cell division) that results from placing tissues and cells into culture. Its purpose is to minimize aging of cells that are used for somatic cell nuclear transfer into mature enucleated oocytes for the purpose of cloning or transgenic animal production. An additional purpose of the technology is to provide a substantial economic benefit by limiting the labor, supplies costs and storage costs associated with generating large numbers of cells prior to the time when cells are needed for nuclear transfer. With this technology it should be possible to generate the relatively small number of cells needed for nuclear transfer while minimizing the amount of cell division. This technology has also been utilized to recover cells post mortem from animals for use in nuclear transfer. Success has been achieved in recovering viable cells from a biopsy collected from a suitably refrigerated animal 6–7 days post mortem and from an animal held in a conventional residential freezer for 4 days.

Most cell types have a limited lifespan in culture that is characterized by the number of cell divisions or population doublings. It is thought that the lifespan may be limited by loss of pieces of DNA called telomeres at the ends of chromosomes because there is a correlation between the aging process and telomere length. However, cellular senescence and aging process is related to more than telomere length alone. Telomeres are the DNA-protein complexes that form the ends of eukaryotic linear chromosomes. These complexes maintain the integrity of genomic DNA by preventing degradation and fusion of chromosome ends and by ensuring complete chromosomal replication. The chromosomal ends are eroded each time the cell replicates its DNA during the process of cell division. Telomere-based models of cellular senescence would predict that nuclear transfer-derived animals would reach a critical telomere length earlier than a normal animal of the same age. Therefore methods to minimize cell division in cells that will be used for the purpose of somatic cell nuclear transfer would minimize telomere loss in addition to other negative effects of cell division.

A paper has been published that shows that telomere lengths were not decreased in cloned calves, but in fact elongated (Lanza et al., 2000), while another paper has been published in which telomere erosion did not appear to be repaired in cloned sheep (Shiels et al., 1999). Regardless of the effect of cloning on telomere loss, cryopreservation methods that minimize cell division are beneficial.

Definitions

An explant is a tissue taken from an animal and transferred to culture medium [Butler and Dawson, 1992].

Passage is the transfer of cells form one culture vessel to another and usually accompanied by cell dilution. The term is synonymous with 'subculture' (Butler and Dawson, 1992).

Viability is a measure of the proportion of live cells in a population (Butler and Dawson, 1992).

Cryopreservation of Tissues and Cells

Techniques are described that provide cells for somatic cell nuclear transfer derived from surgical or biopsy specimens (FIG. 1). The process consists of 3 steps outlined below. These techniques have been successfully applied to the collection of cells from healthy animals and from animals that have been dead for periods ranging from hours to 7 days.

Step 1. Processing of Fresh Tissue for Cryopreservation

Upon arrival in the laboratory, tissue is immediately removed from the shipping container and tubes following decontamination of tubes. Tissue is washed with fresh sterile culture medium suitable for the selected cell type being prepared with 10% Fetal Bovine Serum and antibiotic formulations.

The biopsy or surgical specimen is divided into two parts:
1) One part of the biopsy or tissue specimen is used for direct freezing, without placement into tissue culture.
2) A second part of the biopsy/tissue sample is used for two purposes.
   a. One purpose includes the generation of cells by harvesting cell outgrowths from tissue pieces or dissociation of cells from tissue pieces.
   b. The second purpose is to cryopreserve tissue pieces that have been used for cell explants and/or verification of the viability of tissue pieces and their ability to produce cell outgrowths.

The biopsy is divided into small tissue pieces about 1 mm$^3$. One fraction of pieces is cryopreserved directly by placing tissue for 10 minutes in appropriate culture medium with 10% Fetal Bovine Serum (FBS), antibiotic formulation, plus 10%–20% DMSO. Tissue is then transferred in 1 ml of the same solution to 2.0 ml Nunc or Corning cryotubes and then tissue is frozen at a rate of –1° C./minutes. NAL-GENE™ Cryo 1° C. Freezing Containers (Catalog # 5100-0001) placed in a –80° C. ultracold freezer overnight may be used for this purpose.

The following day the tissues can be rapidly transferred from –80°/C. into liquid nitrogen. Frozen cryotubes are not exposed to air for more than 5 seconds before immersion into liquid nitrogen. Note: If cryopreserved cells or tissue ever rises to –60° C., irreversible injury to cells or tissue will result.

This procedure preserves cells within tissue pieces for subsequent isolation of cells for nuclear transfer without causing cells to divide until cells are ready to be harvested for nuclear transfer. The disadvantage of this procedure is that the viability of cells and their ability to grow in culture is not verified prior to freezing.

Step 2. Culture and Passage of Tissues and Cells

Tissue pieces that are generated from the biopsy or from tissue frozen upon arrival or from tissue previously maintained in culture are placed into suitable culture flasks such as Corning 25 cm$^2$ tissue culture flasks with 7–10 ml of fresh medium and incubated at 37° C. under a 5% $CO_2$ atmosphere with cap loose.

Typically scattered individual cells are seen in the culture dish in two or three days and by 7 to 10 days the flask is ready to be subcultured at which time some cells are placed into new flasks and some cells are cryopreserved as above with each passage.

Alternatively, cells can be dissociated from tissue pieces by a combination of mechanical and enzymatic digestion of tissue pieces to derive a suspension of small groups of cells and single cells. These are transferred to the culture flask with fresh medium and incubated as above. Once these cells proliferate and reach near confluence on the surface of the culture dish, the flask is ready to be subcultured at which time some cells are placed into new flasks and some cells are cryopreserved as above with each passage.

This procedure is routinely applied for the isolation of cells for nuclear transfer and is limited because cells must be propagated in order to generate large stocks of cells that can be frozen and thawed at a later date.

Step 3. Processing of Cultured Tissue Pieces for Cryopreservation

Tissue pieces that have been maintained in culture for several days or longer provide a useful source of explanted cells when needed. The value of cryopreserving tissue pieces that have been cultured for short to long intervals is that unwanted cell divisions that lead to aging and/or senescence can be reduced if tissues are frozen back early. In addition, with sufficient time in culture, it is possible to verify the viability of cells within tissue pieces and their ability to explant when placed into a flask with culture medium. Further, tissues can be repeatedly frozen and thawed and still retain their ability to serve as a reservoir of viable cells because the cryopreservation process will arrest cell division until they are thawed.

Tissue pieces should be no larger than 1 mm$^3$ when they are transferred to 2.0 ml Nunc or Corning cryotubes in appropriate culture media with 10% Fetal Bovine Serum, antiobiotic formulations, and 10%–20% DMSO and incubated for 10 minutes prior to freezing. Tissue is then frozen at a rate of −1° C./minute using NALGENE™ Cryo 1° C. Freezing Containers (Catalog # 5100-001) placed in a −80° C. ultracold freezer overnight. The following day the tissues can be rapidly transferred from −80° C. into liquid nitrogen. Frozen cryotubes are not exposed to air for more than 5 seconds before immersion in liquid nitrogen. Note: If cryopreserved cells or tissue ever rises to −60° C., irreversible injury to cells or tissue will result.

This procedure is advantageous because it can be used to verify the viability of the cells (i.e., tissue pieces can be frozen with the certainty that small populations of viable cells can be derived at any time. The number of cells propagated from the tissue piece can be limited to the number needed in a given nuclear transfer procedure.

Suitable cells for cryopreservation using the present invention comprise bacteria, bacteriophage, fungi, yeast, protozoa, algae, plant cells, animal cells, hybridomas, plant viruses, and animal viruses.

There are numerous media formulations that are suitable for the proliferation and maintenance of cells in culture, several of which appear to support cell growth better than others, depending on the species and cell type. Typical mammalian culture media include, but are not limited to: Basal Medium Eagle (BME), Dulbecco's Modified Eagles Medium (DME), Nutrient Mixture Ham's F-10, Nutrient Mixture Ham's F-12, Dulbecco's Modified Eagles Medium Nutrient Mixture F-12 Ham (DME/F12 1:1 mixture), L-15 Medium Leibovitz, McCoy's 5A Medium, Medium 199, Minimum Essential Medium Eagle (MEM), RPMI-1640 Medium, and Waymouth's Medium.

The following two media formulations are listed as examples that have been successfully utilized for growth of cells from canine, feline, equine, bovine, porcine, caprine, and ovine species.

| HAMS F-12 Media (1000 ml) | DMEM/F12 Media (1000 ml) |
| --- | --- |
| Sigma catalog no. N-4388 | Sigma catalog no D8900 |
| 10 ml PSF antibiotic formulation | 10 ml PSF |
| 1.176 g sodium bicarbonate | 1.176 g sodium bicarbonate |
| adjust pH to 7.25 | adjust pH to 7.25 |
| add appropriate serum volume* | add appropriate serum volume* |
| sterilize by filtration | sterile by filtration |

*Serum is typically used in culture medium at a concentration ranging from 5 to 20%. Fetal bovine serum (FBS) is a preferred serum for growing cells from fresh tissue due to the high concentration of growth factors present. However other sera such as newborn calf serum, horse serum, and others may be used depending upon the cell type and species, and the culture requirements of the cells to be grown.

Cryoprotective agents such as sugars, serum, and solvents may be used. Particularly suitable cryoprotective agents are dimethylsulfoxide (DMSO), glycerol, ethylene glycol, and propanediol.

There are numerous antibiotic formulations used in culture media and buffered saline solutions. Suitable antibiotics include amphotericin B, ampicillin, cephalothin, dihydrostreptomycin, erythromycin, gentamicin sulfate, kanamycin sulfate, lincomycin HCL, neomycin sulfate, nystatin, paromomycin sulfate, penicillin G, penicillin V, polymyxin B sulfate, spectinomycin dihydrochloride, streptomycin sulfate, tetracycline, and tylocin tartrate. A mixture of penicillin, streptomycin, and fungizone (or amphotericin B) is routinely used in the primary culture systems from tissue biopsies in the present invention.

There are numerous containers that may be used for cryopreservation. Flame-sealed glass ampoules or screw-cap plastic vials may be used. Suitable cryopreservation storage vessels are Nunc or Corning cryotubes.

Uniform cooling rates may be obtained by using a programmable-rate cell freezing apparatus. A suitable freezing container is the NALGENE™ 1° C. freezing container.

Buffered saline solutions are typically used either for washing cultures to remove cellular debris or for washing of cells prior to dissociating cells and dislodging them from the culture dish. Phosphate buffered saline (PBS) containing Ca2+ and Mg2+ is used for washing and saline lacking these divalent cations is typically used as a wash prior to dissociating and dislodging cells from the culture dish.

EXAMPLES

The following examples are included to demonstrate preferred embodiments of the invention. It should be appreciated by those of skilled the art that the techniques disclosed in the examples which follow represent techniques discovered by the inventor to function well in the practice of the invention, and thus can be considered to constitute preferred modes for its practice. However, those of skill in the art should , in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1
Surgical Collection of Tissues or Biopsies

1) Anesthesia or Local block

Sedation included intramuscular administration of glycopyrrolate (0.005 mg/lb), oxymorphone (0.05 mg/lb up to a maximum of 4 mg) in the presence or absence of acepromzaine (0.025 mg/lb up to a maximum of 1 mg). Lidocaine (5 mg/kg maximum dose) was used for the skin biopsy local block.

2) Site preparation

Following administration of sedation, an area of the ventral abdominal region near the midline was clipped and prepped with chlorohexidine scrub. The area was covered with a sterile drape. A #10 or 15 blade was used to make an elliptical incision to excise a 2 cm segment of skin or oral mucosa. Appropriate suture material was used for superficial skin.

3) The skin biopsy (approximately 1×3 cm) was obtained from the ventral abdomen in standard aseptic and surgical fashion using an elliptical incision and closed with appropriate suture materials.

4) The oral mucosal biopsy (approximately 0.5×1 cm) was obtained from the inside of the upper lip using an elliptical skin incision and was closed with appropriate suture materials.

5) Tissue collections from other sites followed suitable preparation and involved aseptic collection. Post mortem samples were appropriately prepped and aseptically collected.

Example 2
Kits for Shipping Surgically Collected or Biopsies of Animal Tissues (BioBox™)

1) Kits for shipping viable tissue specimens were shipped to veterinarian in advance of surgery.

2) The BioBox™ contained 4–6 sterile conical centrifuge tubes packaged in a styrofoam insulated shipping container with "blue ice" ice packs. Contents of the tubes included sterile Ham's F12 culture medium with 10% Fetal Bovine Serum plus antibiotic formulation, PSF (penicillin, streptomycin, and fungizone=amphotericin B).

3) This medium was kept refrigerated until tissue collection and was shipped back overnight with the same container and re-frozen ice packs.

Example 3
Processing of Fresh Tissue for Cryopreservation

1) All working surfaces were decontaminated with 70% ethanol.

2) Upon arrival in the laboratory, tissue was immediately removed from the shipping container and tubes following decontamination of tubes. Tissue was washed with fresh sterile culture medium suitable for the species and desired cell type being processed with 10% Fetal Bovine Serum and antibiotics. In the event that proper surgical collection procedures were not followed, tissue decontamination procedures were followed.

The biopsy was separated in half for direct freezing or cell culture. The biopsy is divided into small tissue pieces of about 1–2 mm$^3$. One fraction of pieces was cryopreserved directly by placing tissue for 10 minutes in the Ham's F 12 with 10% Fetal Bovine Serum, antibiotics plus 10% DMSO. Tissue was then transferred in 2 ml of the same solution to 2.0 ml Nunc or Corning cryotubes and then tissue is frozen at a rate of 1° C./minute. We used NALGENE™ Cryo 1° Freezing Containers (VWR Catalog #5100-0001) placed in an −80° C. ultracold freezer overnight.

The second fraction of tissue pieces was placed directly into culture.

3) The following day the tissues were rapidly transferred from −80° C. into liquid nitrogen. Frozen cryotubes were not exposed to air for more than 5 seconds before immersion in liquid nitrogen. Note: If cryopreserved cells or tissue ever rises to −60° C., irreversible injury to cells or tissue will result. Once in liquid nitrogen, cells are logged into the cryobank data base. Abbreviation used for Fresh Frozen Tissue on cryotubes and flasks: FFT.

Example 4
Culture, Harvesting, and Cryopreservation of Cells

1) Tissue pieces generated from the biopsy as described above were further reduced in size (<1 mm$^3$ by cutting with Metzenbaum scissors) in a sterile Petri dish and placed into suitable culture flasks such as Falcon or Corning 25 cm$^2$ or 75 cm$^2$ tissue culture flasks with 6–10 ml of fresh medium for 25 cm$^2$ flask or 12–20 ml of medium for 75 cm$^2$ flask.

2) Tissue pieces were incubated at 37° C. under a 5% $CO_2$ atmosphere with loose cap.

3) Medium was checked daily for cell outgrowth from the tissue pieces (and for contamination).

4) One half of the medium was typically replaced every other day with fresh medium if there was a detectable change in pH or if cell debris is present in cultures. This enhanced cell growth in "conditioned" medium.

5) Typically scattered individual cells were seen in the culture dish in two or three days and by 7 to 10 days the flask was ready to be subcultured.

6) Tissue pieces from flasks to be passaged were transferred to a new flask with fresh media.

7) Some cells were subcultured (passaged) and some cells harvested for cryopreservation with each tissue transfer.

8) Cells to be cryopreserved were resuspended in the appropriate media with 10% FBS, PSF, and 10% DMSO. Density of cells was dependent on application, ranging from 2 million to 100,000/ml. Cells were directly frozen without an incubation period at a rate of −1°C./minute using NALGENE™ Cryo 1° C. Freezing Containers (Catalog # 5100-0001) in a −80° C. ultracold freezer overnight.

9) The following day the cells were rapidly transferred from −80° C. into liquid nitrogen. Frozen cryotubes were not exposed to air for more than 5 seconds before immersion in liquid nitrogen. Note: It cryopreserved cells or tissue ever rises to −60° C., irreversible injury to cells or tissue will result. Once in liquid nitrogen, cells are logged into the cryobank database.

Example 5
Processing of Cultured Tissue Pieces for Cryopreservation

1) Tissue pieces that have been maintained in culture for several days or longer provide a useful source of explanted cells when needed. The value of cryopreserving tissue pieces that have been cultured for short to long intervals is that unwanted cell divisions that lead to aging and/or senescence can be reduced if tissues are frozen back early. In addition, with sufficient time in culture, it is possible to verify the viability of cells within tissue pieces and their ability to explant when placed into a flask with culture medium. Further, tissues can be repeatedly frozen and thawed and still retain their ability to serve as a reservoir of viable cells because the cryopreservation process will arrest cell division until they are thawed.

2) Tissue pieces should be no larger than 1 mm$^3$. Tissues were incubated in the appropriate media with 10% Fetal Bovine Serum, PSF, and 10% DMSO for 10 minutes and then transferred to 2.0 ml Nunc or Corning cryotubes in 1 ml of the freezing medium. Tissue was then frozen at a rate of −1° C./minute using NAL-GENE™ Cryo 1° C. Freezing Containers (Catalog # 5100-0001) placed in an −80° C. ultracold freezer overnight. The following day the tissues can be rapidly transferred from −80° C. into liquid nitrogen. Frozen cryotubes were not exposed to air for more than 5 sec before immersion in liquid nitrogen. Note: It cryopreserved cells or tissue ever rises to −60° C., irreversible injury to cells or tissue will result.

3) Once in liquid nitrogen, cells were logged into the cryobank database. Abbreviation used for Frozen Tissue that has been maintained in culture for some period of time: FT.

Example 6
Retrieval of Tissues or Cells from Cryopreservation

1) Tissue pieces or cells were recovered from cryopreservation and retain high viability if the tissue is maintained at liquid nitrogen temperatures continuously. It is important not to hold ampule out of nitrogen for more than a few seconds at a time when searching for ampule of cells in the cryobank.

2) When retrieving cells or tissue pieces, the laminar flow hood was decontaminated and all media warmed and culture dishes were ready.

3) The ampule was removed from liquid nitrogen and dropped directly into a 37° C. water filled beaker (~500 ml) to provide a large heat sink. Cells were rapidly thawed by gently swirrelling ampule with fingers around the water to facilitate rapid warming.

4) Once thawed, outside of cryotube was decontaminated only after recording all data listed on the cryotube. Solvents can remove information on label.

5) Thawed cells were gently resuspended in at least 10 ml of fresh medium without DMSO and medium was placed with cells/tissue in a 25 cm$^2$ flask with 7–10 ml of media or with 20 ml in 75 cm$^2$ tissue culture flask. Thawed tissues were transferred to 10 ml of fresh medium without DMSO in a conical centrifuge tube to eliminate DMSO. Tissue pieces were collected by velocity sedimentation at unit gravity or gentle centrifugation then resuspended in fresh medium before transfer to the flask. The flask was returned to incubator at 37° C. under a 5% CO$_2$ atmosphere with cap loose.

6) Depending on the rate of plating, media containing residual DMSO was replaced with fresh medium as soon as possible, but at the latest, within 8 hr.

7) All information on flask was recorded including passage number, transfer no., the number of times the tissue piece has been frozen and thawed, etc.

Abbreviations used on flask for Fresh Frozen Tissue (FFT) and tissue cultured prior to freezing, i.e., Frozen Tissue (FT).

Example 7
Cell Harvesting Protocol

1) Aspirate old media from flask.

2) Cells were rinsed with PBS without Ca$^{2+}$ and Mg$^{2+}$ for 30 seconds.
PBS without Ca2+ & Mg2+ (1000 ml) [for rinsing before harvesting cells from culture dish]
Sigma catalog no. D-5652 (without calcium chloride and magnesium chloride)
adjust to pH to 7.25
sterilize by filtration 3) PBS without Ca$^{2+}$ and Mg$^2$ was aspirated from flask.

4) Trypsin-EDTA solution was added to flask.
3.0 ml for 75 cm$^2$ flask or 1.0–1.5 ml for 25 cm$^2$ flask
Trypsin-EDTA Solution for Releasing Anchored Cells from Culture Dish (40 ml)
To 32 ml of PBS without Ca2+ & Mg2+ in a sterile bottle, added:
2 ml 7.5% sterile sodium bicarbonate solution
4 ml trypsin EDTA stock solution (10×, Boehringer Mannheim Catalog # 1074 474
2 ml PSF# stock
Add Sodium Bicarbonate to PBS before other ingredients to protect other proteins from pH fluctuation.

5) Cells were released (cells will usually detach from the culture dish within 5 minutes). Trypsin was rocked over cells and side of flask was periodically tapped to determine extent of cell detachment. When the majority of cells were dislodged, flask was given a sharp slap on the side. This removed residual cells.

6) Sufficient media containing serum was quickly added to bring contents of flask to 10 ml total volume. Trypsin did not sit on cells for an extended period of time. This will compromise cultures. The remaining cells were washed from bottom of dish by pipetting cell suspension over the surface.

7) Media (with cells) was transferred to sterile centrifuge tube. Aliquot (20 1) was immediately removed and placed in cuvette for counting with Coulter Counter.

8) The aliquot was counted with Coulter Counter or hemacytometer

9) Cells were resuspended at 1 million cells per ml and distribute to flasks, culture dishes, or freeze in 10% DMSO as needed.
T25 flasks hold about 7 ml
T75 flasks hold about 20 ml
T150 flasks hold about 40 ml
2 well Lab-Tek slides about 100K cells in 1.5 ml/well 10) Cells were incubated at 37° C. under a 5% CO$_2$ atmosphere with cap loose.

Figure 2:
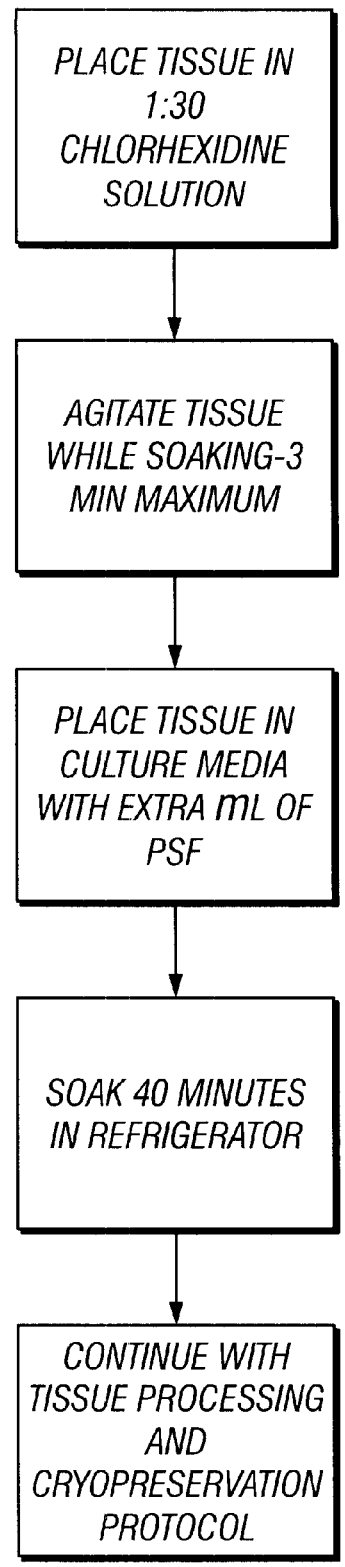
FIG. 2 Diagram of tissue decontamination protocol.

Example 8
Tissue Decontamination (FIG. 2)

1) About 20 ml of 1:30 chlorhexidine solution was placed in a 100 mm$^2$ petri dish.

2) Media was removed from tissues.

3) Tissues were placed in chlorhexidine for 2–3 minutes ONLY.

4) Tissues were agitated, while soaking, with sterile forceps.

5) Tissues were placed in 50 ml conical tube with 20 ml of Ham's/F-12 & 1 ml extra of PSF.

6) TISSUES WERE SOAKED in the culture medium for 40 minutes in the refrigerator.

7) Tissues were placed in hood, and regular tissue isolation and culture procedures were performed.

REFERENCES

The following references, to the extent that they provide exemplary procedural or other details supplementary to those set forth herein, are specifically incorporated herein by reference:

Abir R, B Fisch, A Raz, S Nitke, and Z Ben-Rafael (1998) Preservation of fertility in women undergoing chemotherapy: Current approach and future prospects. Journal of Assisted Reproduction and Genetics 15: 469–477.

Butler M and Dawson M, eds, Cell Culture (Lab Fax), Bios Scientific Publishers, Academic Press, Oxford, 1992.

de Kanter R, Olinga P, Hof I, de Jager M., Verwillegen W A, Slooff M J, Koster H J, Meijer D K, Groothuis G M (1998) A rapid and simple method for cryopreservation of human liver slices. Xenobiotica 28(3): 225–34.

Gianaroli L, Magli M C, Selman H A, Colpi G, Belgrano E, Trombetta C, Vitali G, Ferraretti A P (1999) Diagnostic testicular biopsy and cryopreservation of testicular tissue as an alternative to repeated surgical openings in the treatment of azoospermic men. Hum Reprod 14(4): 1034–8.

Lanza R P, Cibelli J B, Blackwell C, Cristofalo V J, Francis M K, Barlocher G M, Mak J, Schwertzer M, Chavez E A, Sawyer N, Lansdorp, P M, and West M D. Extension of Cell Life-Span and Telomere Length in Animals Cloned from Senescent Somatic Cells. Science 2000288, 665–669.

Oktay K, H Netwon, Y Aubard, O Salha, and R G Gosden (1998) Cryopreservation of immature human oocytes and ovarian tissue—an emerging technology? Fertility and Sterility 69: 1–7.

Shiels P G, Kind A J, Campbell K H, Waddington D, Wilmut I, Colman A, and Schnieke A E. Analysis of telomere lengths in cloned sheep. Nature 1999 399, 316–317.

Sheridan R, Mahe J, Waters P (1998) Autologous skin banking. Bums 24:46–48.

Simione, F. P. (1998) Cryopreservation Manual, Nalge Nunc Intemation Corporation, Rochester, N.Y.

Sommer M., Funfstuck R, Stein G (1999) Cell cultures from cryopreserved renal biopsies and other tissue samples. Exp. Toxic Pathol 51: 229–234.

Wusteman M C, Armitage J W, Wang L H, Busza A L, Pegg D E (1999) Cryopreservation studies with porcine corneas. Curr Eye Res 1999 Sep; 19(3): 228–233.

Zieger M A, Woods E J, Laker J R, Liu J, Critser J K (1999) Osmotic tolerance limits of canine pancreatic islets. Cell Transplant 1999 May–June; 8(3): 277–84.

We claim:

1. A process for preserving viable tissue or cells comprising:
   a. obtaining a tissue specimen;
   b. dividing the tissue specimen into at least two portions;
   c. cryopreserving directly at least one portion of the tissue specimen to minimize cell division;
   d. culturing at least one of the remaining portions in order to propagate cells from the tissue and verify their viability;
   e. cryopreserving cells obtained from outgrowth or passage of the cultured tissue portion;
   f. cryopreserving the cultured tissue portion once the desired amount or number of cells have been obtained through outgrowth or passage.

2. The process of claim 1, wherein the cryopreservation of the cultured tissue portion occurs simultaneously with the cryopreservation of the cells.

3. The process of claim 1, wherein the cryopreservation of the cultured tissue portion occurs after the cryopreservation of the cells.

4. The process of claim 1, wherein the process is used for preserving viable tissues and cells for use in nuclear transfer.

5. The process of claim 1, wherein said tissue is that of a domestic, exotic, or food animal.

6. The process of claim 1, wherein said tissue is that of a mammal.

7. The process of claim 1, wherein said tissue is that of a dog, cat, horse, sheep, goat, or cow.

8. The process of claim 1, wherein said tissue specimen is that of a dog or cat.

9. The process of claim 1, wherein the tissue specimen is divided into less than or about 1 millimeter$^3$ portions.

10. The process of claim 1, wherein cells or tissue to be cryopreserved are placed in a medium comprising less than or equal to 95% Basal Medium Eagle (BME), Dulbecco's Modified Eagles Medium (DME), Nutrient Mixture Ham's F-10, Nutrient Mixture Ham's F-12, Dulbecco's Modified Eagles Medium Nutrient Mixture F-12 Ham (DME/F12 1:1 mixture), L-15 Medium Leibovitz, McCoy's 5A Medium, Medium 199, Minimum Essential Medium Eagle, RPMI-1640 Medium, or Waymouth's Medium.

11. The process of claim 10, wherein the medium further comprises about 5–20% Fetal Bovine Serum, at least 100 Units/milliliter penicillin, at least 0.1 milligrams/milliliter streptomycin, at least 0.25 micrograms/milliliter amphotericin B, and 10%–20% dimethylsulfoxide.

12. The process of claim 10, wherein said tissue portions or cells are placed in said medium for about 10 minutes before cryopreservation.

13. The process of claim 11, wherein said tissue portions or cells are placed in said medium for about 10 minutes before cryopreservation.

14. The process of claim 10, wherein said tissue portions or cells are placed in said medium directly before cryopreservation.

15. The process of claim 11, wherein said tissue portions or cells are placed in said medium directly before cryopreservation.

16. The process of claim 1, wherein cells or tissue portions to be cultured are placed in a medium comprising less than or equal to 95% Basal Medium Eagle (BME), Dulbecco's Modified Eagles Medium (DME), Nutrient Mixture Ham's F-10, Nutrient Mixture Ham's F-12, Dulbecco's Modified Eagles Medium Nutrient Mixture F-12 Ham (DME/F 12 1:1 mixture), L-15 Medium Leibovitz, McCoy's 5A Medium, Medium 199, Minimum Essential Medium Eagle, RPMI-1640 Medium, or Waymouth's Medium.

17. The process of claim 16, wherein the medium further comprises from about 5–20% Fetal Bovine Serum, at least 100 Units/milliliter penicillin, at least 0.1 milligrams/milliliter streptomycin, and at least 0.25 micrograms/milliliter amphotericin B.

18. The process of claim 1, wherein tissues or cells are frozen at a rate of about −1° C./minute.

19. The process of claim 1, further comprising placing said tissue portions or cells in an −80° C. freezer overnight and transferring said tissue portions or cells into liquid nitrogen the next day.

20. The process of claim 1, wherein after initial cryopreservation and before thawing is desired, the temperature of said tissue portions or cells does not exceed −60° C.

21. A process for preserving viable tissue or cells comprising:
   a. obtaining a tissue specimen;
   b. incubating all or part of said tissue in an about 1:30 chlorhexidine solution for not more than about 3 minutes;
   c. agitating the tissue during the incubation period;
   d. placing the tissue into a medium comprising Ham's F-12 and at least 600 Units/milliliter penicillin, at least 5 milligrams/milliliter streptomycin, and at least 1.5 micrograms/milliliter amphotericin B;
   e. soaking the tissue for about 40 minutes at about 4° C.;
   f. dividing the tissue into at least two portions;
   g. cryopreserving directly at least one portion of the tissue to minimize cell division;
   h. culturing at least one of the remaining portions in order to propagate cells from the tissue and verify their viability;
   j. cryopreserving cells obtained from outgrowth or passage of the cultured tissue portion;
   k. cryopreserving the cultured tissue portion one the desired amount or number of cells have been obtained through outgrowth or passage.

* * * * *